(12) United States Patent
Donaldson et al.

(10) Patent No.: US 7,837,937 B2
(45) Date of Patent: Nov. 23, 2010

(54) BIOLOGICAL AGENT DETECTOR

(75) Inventors: William S. Donaldson, LaVerne, CA (US); Richard K. Chun, Alhambra, CA (US)

(73) Assignee: Hamilton Sundstrand Corporation, Rockford, IL (US)

( * ) Notice: Subject to any disclaimer, the term of this patent is extended or adjusted under 35 U.S.C. 154(b) by 1518 days.

(21) Appl. No.: 11/174,925

(22) Filed: Jul. 5, 2005

(65) Prior Publication Data

US 2007/0189929 A1    Aug. 16, 2007

Related U.S. Application Data

(60) Provisional application No. 60/586,902, filed on Jul. 9, 2004.

(51) Int. Cl.
*G01N 21/00* (2006.01)
(52) U.S. Cl. .................. 422/58; 422/78; 436/155
(58) Field of Classification Search ............ 422/58, 422/78; 436/155
See application file for complete search history.

(56) References Cited

U.S. PATENT DOCUMENTS 3,754,868 A    8/1973    Witz et al.

FOREIGN PATENT DOCUMENTS

| DE | 102 11 655 | 10/2003 |
|----|-----------|---------|
| EP | 0 447 158 | 9/1991 |
| JP | 7-006729 | 1/1995 |
| JP | 2004-520576 | 7/2004 |
| WO | WO 02/29380 | 4/2002 |
| WO | WO 03/100382 | 12/2003 |

OTHER PUBLICATIONS

Sandia Report Jan. 2003, "Miniature Sensors for Biological Warfare Agents using Fatty Acid Profiles". pp. 16, 41.*
Challinor et al, "A rapid simple pyrolysis derivatisation gas chromatography-mass spectrometry method for profiling of fatty acids in trace quantities of lipids", Journal of Analytical and Applied Pyrolysis 1996, vol. 37, pp. 185-197).*
Vreeken et al, "Membrane interface for the direct coupling of pyrolysis and mass spectrometry", Analytica Chimica Acta, 1995, vol. 313, pp. 237-241.*
European Search Report dated Nov. 3, 2005.
K.J. Voorhees et al. "The use of biomarker compounds for the identification of bacteria by pyrolysis-mass spectrometry," Journal of Analytical and Applied Pyrolysis, vol. 40-41, May 1997, pp. 111-134.
Japanese Office Action mailed Feb. 24, 2009.
Japanese Office Action mailed on Jul. 8, 2008.

* cited by examiner

*Primary Examiner*—Lyle A Alexander
*Assistant Examiner*—Dennis M White
(74) *Attorney, Agent, or Firm*—Carlson, Gaskey & Olds (57) ABSTRACT

A biological agent detector detects the presence of any biological agents, such as anthrax or other biological warfare agents, in a sample of air. The biological agent detector includes a bio-concentrator that concentrates an aerosol and a pyrolyzer portion including two detecting devices. One detecting device operates in a sample collection mode and collects a sample of air when the other detecting device operates in a sample analysis mode and analyzes a sample of air. After a predetermined amount of time, the detecting devices switch functions, providing continuous sampling of air.

22 Claims, 5 Drawing Sheets

BIOLOGICAL AGENT DETECTOR

REFERENCE TO RELATED APPLICATIONS

This application claims priority to U.S. Provisional Application No. 60/586,902, which was filed on Jul. 9, 2004.

BACKGROUND OF THE INVENTION

The present invention relates generally to a biological agent detector including two detecting devices that each alternate between a sample collection mode and a sample analysis mode to provide continuous aerosol collection and air monitoring for biological agents.

As an example biological agent detector, a Chemical Biological Mass Spectrometer Block II (CBMS II) detects biological agents present in the air by employing a two-step process using a detector including a pyrolyzer and an associated mass spectrometer. During sample collection, a first pump draws 330 liters of air per minute into an inlet of a bio-concentrator. The bio-concentrator extracts aerosol particles that are drawn into the pyrolyzer by a second pump at 1 liter per minute. The aerosol drawn into the pyrolyzer includes secondary particles, such as dust, fibers, and dirt, and may also include biological agents, such as anthrax or other biowarfare agents. A sample of the aerosol collects at the bottom of a pyrotube in the pyrolyzer. The air and aerosol particles not collected in the pyrotube are exhausted through an exhaust outlet.

During sample analysis, the aerosol sample collected at the bottom of the pyrotube is analyzed to identify any biological agents in the air. A small droplet of a methylating reagent, such as tetramethylammonium hydroxide (TMAH) dissolved in methanol, is added to the air sample with a hypodermic needle. The hypodermic needle is typically made of stainless steel. If the sample includes any biological agents, the methylating reagent derivatizes organic materials to make them more volatile. For example, fatty acids in the cell walls of the bacterial agents form Fatty Acid Methylated Esters (FAMEs).

The sample in the pyrotube is then rapidly heated or pyrolyzed to form gas molecules during an analysis phase. A third pump draws 1 milliliter per second into the mass spectrometer for identification of any biological agents. Biological agents have distinctive patterns of organic molecules. If any biological agents are present in the sample, the mass spectrometer identifies the biological agents by determining the molecular pattern. After a molecular pattern is determined, the pattern is compared to a pre-programmed list of patterns for identification of any biological agents in the air sample.

A drawback to the prior art biological agent detector is that the prior art system must stop collection of an aerosol sample in the pyrotube during the analysis phase, and therefore does not detect any biological agents present in the air during sample analysis. Therefore, the sample collection is intermittent, with time gaps in which no air monitoring occurs. This increases the time required to detect the presence of any biological agents and in some situations may result in a failure to detect a transient agent.

To provide continuous detection and analysis, a second pyrolyzer and bio-concentrator are needed. However, duplicating the bio-concentrator and the pyrolyzer is expensive.

Thus, it is desirable to have a biological agent detector including two detecting devices that share a bio-concentrator and that each alternate between a sample collection mode and a sample analysis mode to provide continuous collection and monitoring of an air sample, as well as overcoming the other above-mentioned deficiencies of the prior art.

SUMMARY OF THE INVENTION

A biological agent detector detects the presence of any biological agents, such as anthrax or other biological warfare agents, in a sample of air. The biological agent detector includes a bio-concentrator that concentrates an aerosol within the sample of air and a pyrolyzer portion including two detecting devices. One detecting device operates in an aerosol sample collection mode and extracts the aerosolized particles from the sample of air when the other detecting device operates in a sample analysis mode and analyzes the particles collected from a previous sample of aerosol. After a predetermined amount of time, the detecting devices switch functions.

The bio-concentrator draws air into the biological agent detector through an inlet and separates aerosol particles from the main airflow. The bulk of the air is exhausted through an exhaust. The bio-concentrator is moveable so that a concentrated aerosol outlet of the bio-concentrator is alignable with an inlet of each of the detecting devices. Physically moving the bio-concentrator so that the concentrator aerosol outlet aligns with the inlets of each of the detecting devices permits an uninterrupted flow of concentrated aerosol from the bio-concentrator to the detecting device with no sharp bends or discontinuities in the flow path.

When the concentrated aerosol outlet of the bio-concentrator is aligned with a first detecting device, the sample concentrated in the bio-concentrator flows along a stainless steel inlet tube and collects in a closed end quartz pyrotube in the first detecting device.

When the air sample is being collected in the first detecting device, an air sample previously collected in the second detecting device is analyzed. A small droplet of a methylating reagent, such as 0.0015 Molar to 0.015 Molar TMAH dissolved in methanol, is added to the sample collected in the pyrotube. The methylating reagent splits open the cells of any bacterial agents in the sample and neutralizes and derivatizes the organic molecules in the agents to more volatile compounds. The sample is also heated to form pyrolysis products.

The pyrolysis products are transported from the pyrotube to a mass spectrometer for identification and analysis. The mass spectrometer includes a preprogrammed list of molecular patterns that are each associated with a specific biological agent. If any biological agents are present the sample, the mass spectrometer identifies the biological agents by comparing the identified molecular pattern to the list of molecular patterns preprogrammed into the mass spectrometer. After a match is found, the mass spectrometer identifies the associated biological agent.

After a predetermined amount of time, the functions of the detecting devices are switched. The bio-concentrator moves so that the concentrated aerosol outlet is aligned with the inlet of the second detecting device for collection of an aerosol sample. Therefore, the biological agent detector continuously collects an air sample for analysis.

These and other features of the present invention will be best understood from the following specification and drawings.

BRIEF DESCRIPTION OF THE DRAWINGS

The various features and advantages of the invention will become apparent to those skilled in the art from the following detailed description of the currently preferred embodiment. The drawings that accompany the detailed description can be briefly described as follows.

DETAILED DESCRIPTION OF THE PREFERRED EMBODIMENT

Figure 1:
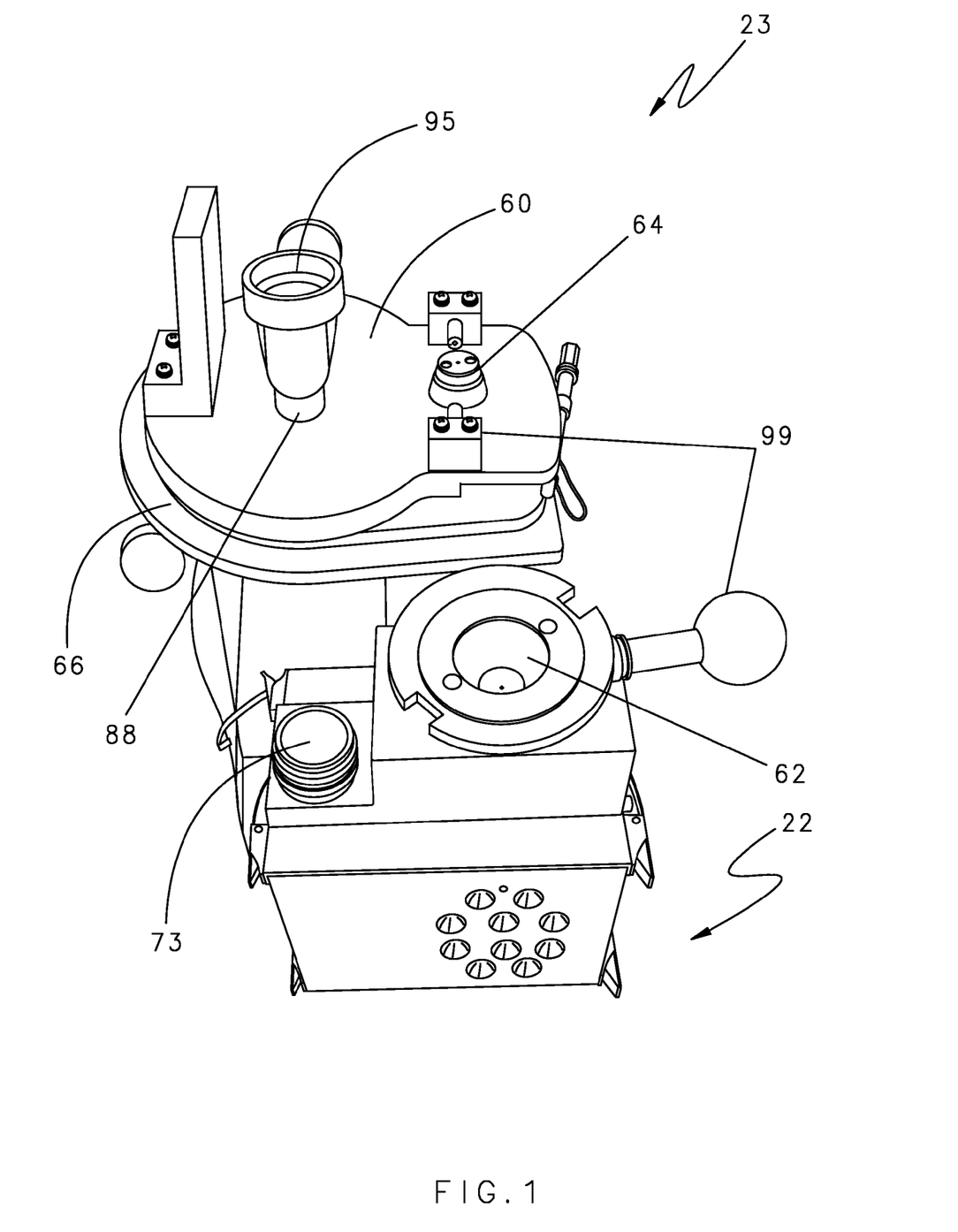
FIG. 1 illustrates a bio-concentrator and an aerosol flow switch mechanism of a biological agent detector.

FIG. 1 illustrates a bio-concentrator 22 and an aerosol flow switch mechanism 23 of a biological agent detector 20 of the present invention. The biological agent detector 20 detects the presence of any biological agents, such as anthrax or other biological warfare agents, in a sample of air.

The bio-concentrator 22 concentrates an aerosol from an air stream and provides the aerosol to one detecting device 26a and 26b of a pyrolyzer portion 21 for collection and analysis. The aerosol flow switch mechanism 23 provides the aerosol to one of the detecting devices 26a and 26b, while the aerosol sample in the other of the detecting devices 26a and 26b is analyzed.

Figure 4A:
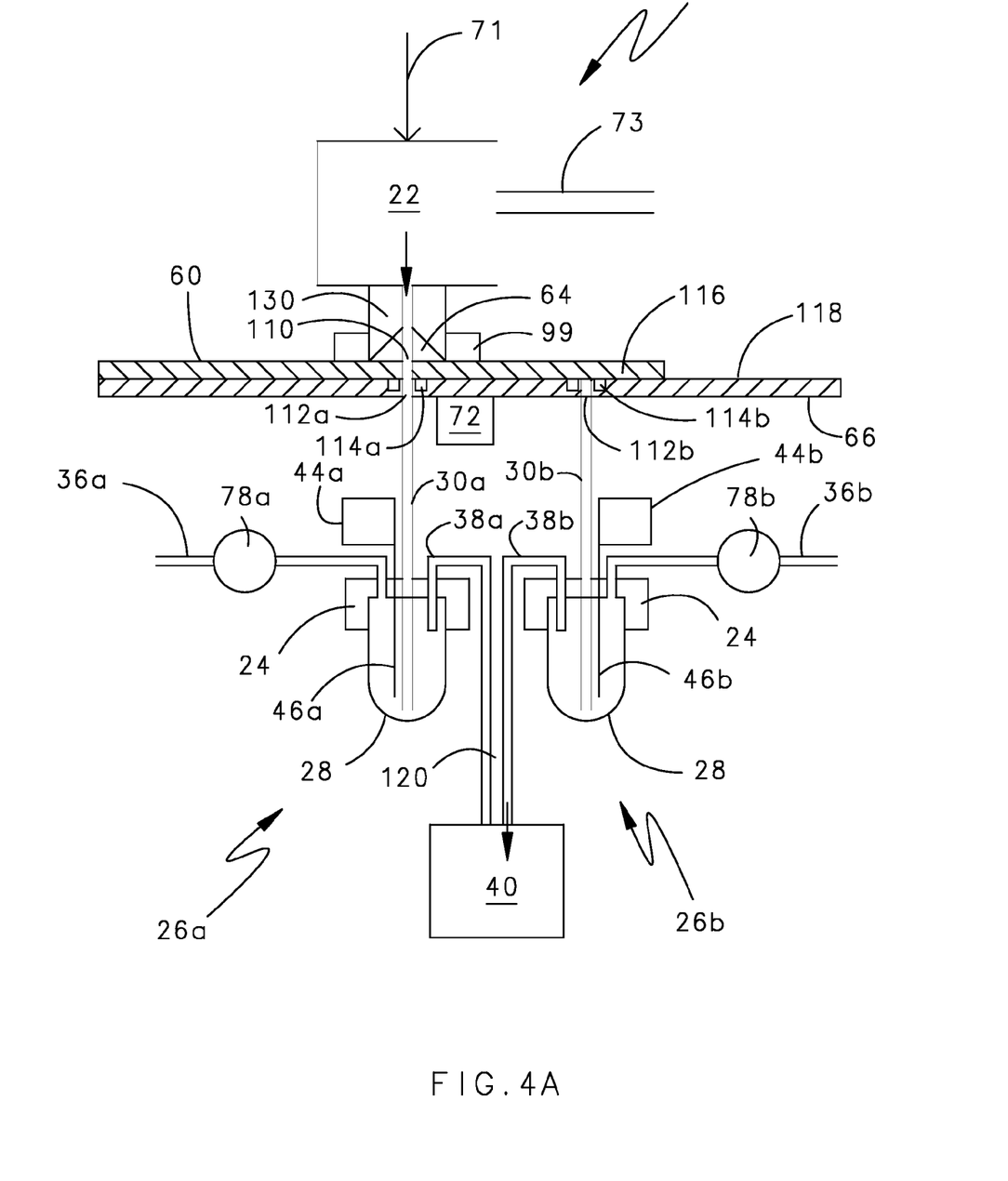
FIGS. 4A and 4B illustrates movement of bio-concentrator from a first position when it aligns with one detecting device to a second position where it aligns with the other detecting device.
Figure 4B:
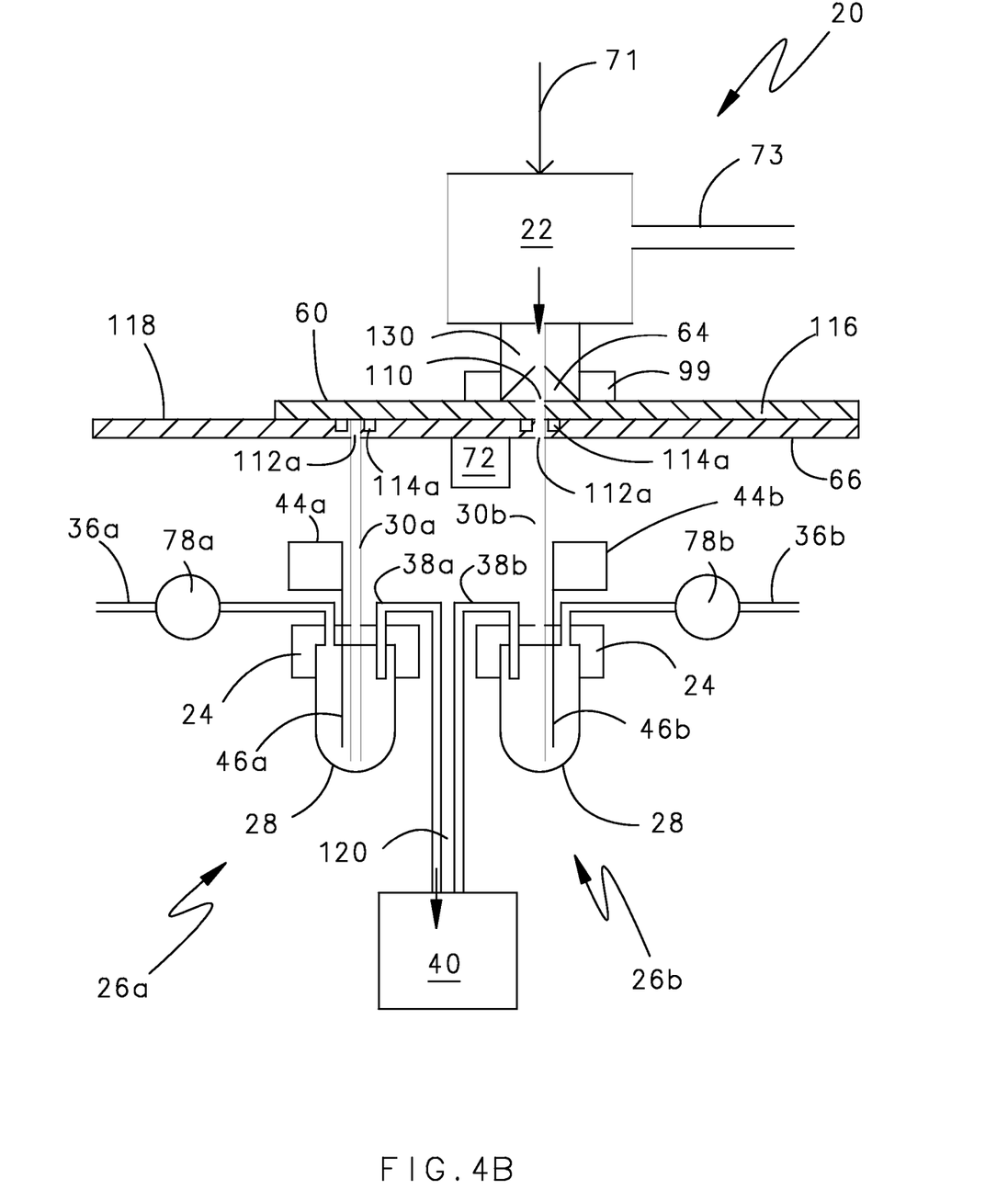

The bio-concentrator 22 draws over 300 liters of air per minute into the biological agent detector 20 through an inlet 71 (shown in FIGS. 4A and 4B). The bio-concentrator 22 separates aerosol particles from the main airflow and exhausts the bulk of the air through an exhaust 73 and an aligned exhaust port 95 at approximately 299 liters/minute. The bio-concentrator 22 provides a concentrated airflow of approximately 1 liter per minute containing almost the entire aerosol of interest through a concentrated aerosol outlet 62 that leads to one of the detecting devices 26a and 26b for collection. The concentrated airflow contains about 90% of the bio-particles.

The bio-concentrator 22 is clamped on a turntable 60 rotatable about a pivot 88. The bio-concentrator 22 is moveable between two positions. The concentrated aerosol outlet 62 is alignable with one detecting device 26a in a first position and the other detecting device 26b in a second position. The air stream from the concentrated aerosol outlet 62 flows through a small hole 110 in the turntable 60 that is aligned with the concentrated aerosol outlet 62. The turntable 60 rests on and is rotatable relative to a stainless steel base plate 66.

The base plate 66 includes two holes 112a and 112b that are each aligned with one of the detecting devices 26a and 26b, respectively. When the turntable 60 rotates, the small hole 110 in the turntable 60 aligns with one of the holes 112a and 112b in the base plate 66. The sidewalls of the holes 112a and 112b are polished to eliminate the possibility of discontinuities in the walls of the aerosol path. An upper surface 118 of the base plate 66 includes a groove that surrounds each of the holes 112a and 112b, and a rubber o-ring 114a and 114b is received in each of the grooves to provide a relatively air tight seal between the upper surface 118 of the base plate 66 and the lower surface 116 of the turntable 60.

The base plate 66 includes hardened steel pins that penetrate grooves in the turntable 60 to limit rotation of the turntable 60 and to provide a precise stop so that the hole 110 in the turntable 60 aligns with one of the two holes 112a and 112b in the base plate 66. A compression spring 72 (shown in FIGS. 4A and 4B) provides 10 pounds of force between the turntable 60 and the base plate 66 to ensure that the o-rings 114a and 14b are compressed and that the lower surface 116 of the turntable 60 contacts the upper surface 118 of the base plate 66. The precise alignment stops and the compression force ensures a smooth path for the aerosol stream with minimum discontinuities in the sidewalls of the holes 112a and 112b.

The upper surface of the turntable 60 includes a conical alignment feature 64 feature that mates with a conical aperture 130 in the lower surface of the bio-concentrator 22 to ensure that the concentrated aerosol outlet 62 of the bio-concentrator 22 is precisely aligned with the through hole 110 in the turntable 60. A locking mechanism 99 locks the bio-concentrator 22 in position.

As shown in FIGS. 4A and 4B, a motor 70 with a reduction gearbox, a crank and a pushrod rotates the turntable 60 approximately 180° between the first position and the second position. Micro-switches detect the position of the crank. The crank rotates to move the turntable 60 so that the concentrator exhaust outlet 62 of the bio-concentrator 22 precisely aligns with one of the detecting devices 26a and 26b. A solenoid lifts the turntable 60 from the base plate 66 and the o-rings 114a and 114b before the turntable 60 moves to eliminate wear on the o-rings 114a and 114b. When the hardened steel pin precision end stops prevent the turntable 60 from moving, the solenoid is deactivated and the compression spring 72 pushes the turntable 60 back down against the base plate 66. The mechanism that switches the bio-concentrator 22 outlet aerosol flow between the two detecting devices 26a and 26b operates without compromising the aerosol concentration. To efficiently transport the aerosol, several precautions must be taken. The airflow path must be as smooth as possible. Unnecessary turbulence will cause the particles to be thrown against the sidewalls of the transport tubing. Sharp turns in the particle flow path will also cause the particles to be impacted against the sidewalls.

Figure 2:
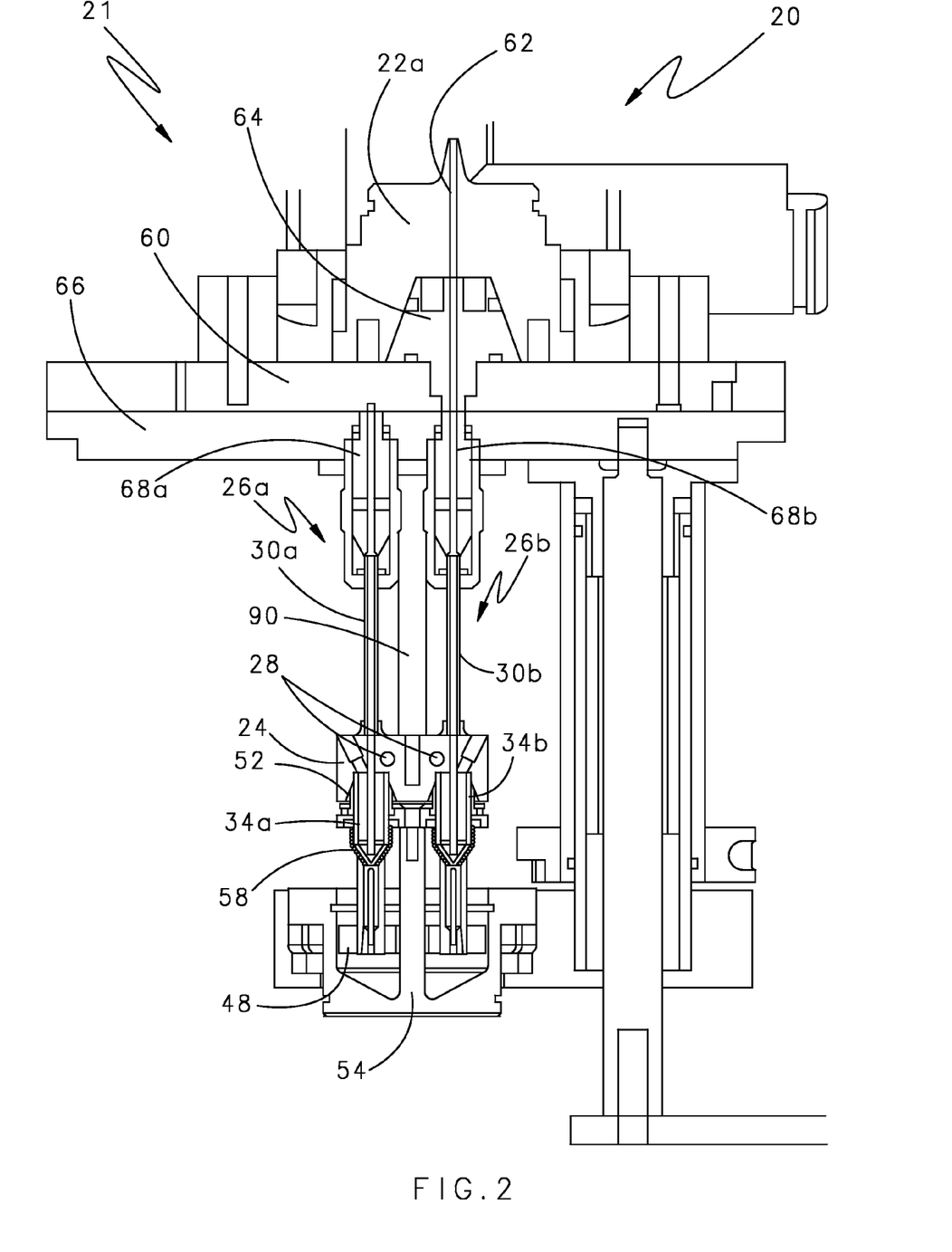
FIG. 2 illustrates a front view of a pyrolyzer portion of the biological agent detector including two detectors.

FIG. 2 schematically illustrates the pyrolyzer portion 21 of the biological agent detector 20 and an interface 22a with the bio-concentrator 22. The pyrolyzer portion 21 includes a body portion 24 and support rods (not shown) that support the body portion 24. The pyrolyzer portion 21 includes the two detecting devices 26a and 26b. In one example, the detecting devices 26a and 26b are pyrolyzers. The body portion 24 includes an embedded heater and temperature sensor device 28. The pyrolyzer portion 21 are attached to an underside of the base plate 66 such that the moveable bio-concentrator 22 is located above the base plate 66.

Figure 3:
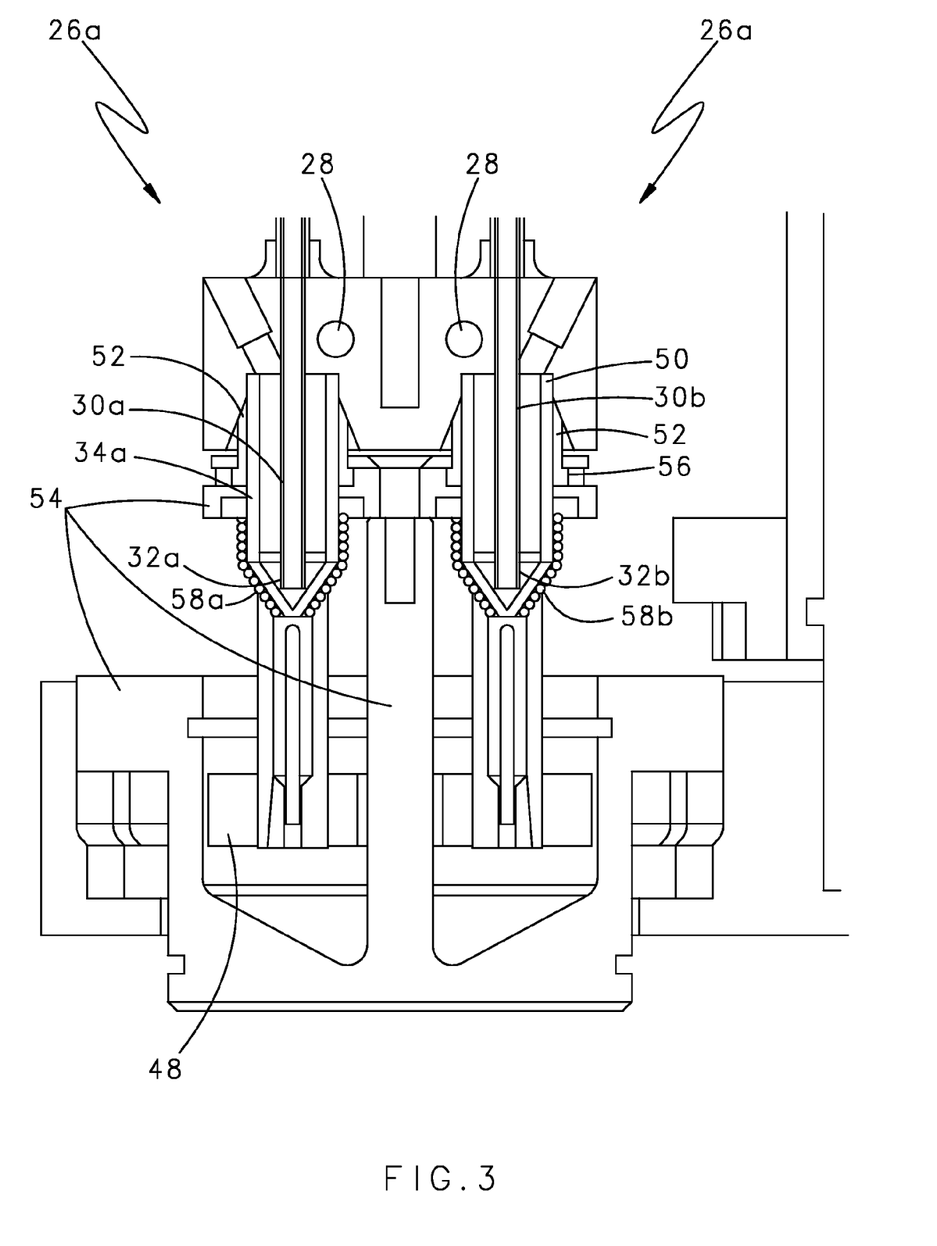
FIG. 3 illustrates an enlarged front view of the pyrolyzer portion of FIG. 2.

Each detecting device 26a and 26b includes a stainless steel inlet tube 30a and 30b, respectively. Each inlet tube 30a and 30b includes a gradually tapered adapter 68a and 68b that increases the airflow velocity in the inlet tubes 30a and 30b. The inlet tubes 30a and 30b are made of an electrically conducting material that is electrically grounded to prevent electrostatic buildup. The inlet tubes 30a and 30b are electropolished to smooth and passivate the internal surfaces. The inlet tubes 30a and 30b are not an integral part of the body portion 24 and can be removed for cleaning and replacement.

The sample air exits the inlet tubes 30a and 30b through an outlet 32a and 32b, respectively, and collects in a respective closed end quartz pyrotube 34a and 34b. The pyrotubes 34a and 34b each have a substantially conical bottom that provides a small collection volume for the sample. The diameter of the inlet tubes 30a and 30b forces approximately 1 liter per minute of aerosol flow to form a jet that impacts the internal vertex of the pyrotube 34a and 34b. The particles carried by the airflow are impacted against the internal closed end of the pyrotube 34a and 34b whereas the air is exhausted. The efficiency of particle impaction and collection requires close tolerances between the tip of the inlet tubes 30a and 30b and the bottom of the pyrotubes 34a and 34b.

Each detecting device 26a and 26b includes a wide stainless steel aerosol outlet exhaust line 36a and 36b that carries an exhaust flow at approximately 1 liter per minute. The wide diameter of the exhaust line 36a and 36b prevents fibrous and other particles that fail to impact and collect at the closed end of the pyrotube 34a and 34b from building up and clogging the exhaust lines 36a and 36b.

A injector needle 46a and 46b adds a small droplet (1 to 2 microliters) of a methylating reagent from a reagent source 44a and 44b (shown in FIGS. 4A and 4B) to the sample collected in the pyrotube 34a and 34b. In one example, the methylating reagent is 0.0015 Molar to 0.015 Molar TMAH dissolved in methanol. The injector needles 46a and 46b are positioned to deliver a methylating reagent droplet to the bottom-center of the respective pyrotube 34a and 34b. The methylating reagent splits open the cells of any bacterial agents in the sample and neutralizes and derivatizes the organic molecules in the agents to more volatile compounds. The injector needles 46a and 46b are a fused quartz capillary tube. The quartz is inert and resistant to the thermal cycling of the detecting devices 26a and 26b and the corrosive methylating reagent.

Each detecting device 26a and 26b is fitted with an injector needle port that seals the injector needle 46a and 46b at the point of entry into the body portion 24. The needle port is connected to the body portion 24 with a thin wall of stainless steel tubing, and the needle ports are angled to provide a clear path to the bottom of the pyrotubes 34a and 34b. The tubing provides thermal resistance and allows the injector needles 46a and 46b to be maintained at a temperature lower than the temperature of the body portion 24. The injector needles 46a and 46b do not touch the sidewalls of the respective pyrotube 34a and 34b to maintain the injector needles 46a and 46b at a lower temperature than the detecting devices 26a and 26b. This provides for reliable methylating reagent metering and delivery. The body portion 24 is hot (approximately 230° C.), and the tubing keeps the needle port cool.

Each detecting device 26a and 26b includes a sample line 38a and 38b, respectively. During sample analysis, the sample lines 38a and 38b transport gaseous pyrolysis products from the pyrotubes 34a and 34b to a mass spectrometer 40 for analysis and identification. The sample lines 38a and 38b are stainless steel and lined with a fused quartz capillary liner. The quartz provides an inert medium for the reliable transport of the pyrolysis products to the mass spectrometer 40. The quartz is also resistant to the corrosive methylating reagent injected into the pyrotubes 34a and 34b during analysis. The quartz capillary liner may be positioned near the bottom of each pyrotube 34a and 34b to maximize the collection efficiency of the pyrolysis products.

Returning to FIG. 2, a spring loaded pyrotube lifting device 48 biases the pyrotubes 34a and 34b against the body portion 24 to prevent any clearance between a top edge 50 of the pyrotubes 34a and 34b and the body portion 24. Pushing the pyrotubes 34a and 34b fully home ensures that the gap between the pyrolyzer internal vertex and the ends of the pyrolyzer inlet tubes 30a and 30b remains constant. The top edge 50 is fire-polished to reduce internal stresses to prevent fractures when pushed against the body portion 24.

A cylindrical ferrule 52 provides a compression seal between the pyrotubes 34a and 34b and the body portion 24. The ferrule 52 is sold under the trademark VESPEL® and sold by E. I. Du Pont De Nemours and Company of Wilmington, Del. A second spring-loaded ferrule-lifting device 54 concentric with the pyrotube lifting device 48 applies pressure to the ferrule 52 to provide a pneumatic seal. The ferrule-lifting device 54 operates independently of the pyrotube lifting device 48. The ferrule-lifting device 54 applies a greater amount of force to the ferrule 52 than the pyrotube-lifting device 48 applies to the pyrotubes 34a and 34b. The pyrotube lifting device 48 pushes the pyrotubes 34a and 34b against the ferrule 52 to form a seal. A step 56 around the lower edge of the ferrule 52 engages a notch of the ferrule-lifting device 54. The ferrule-lifting device 54 can be lowered to remove the ferrule 52 from the biological agent detector 20.

A cylindrical heater 58a and 58b closely contoured to the bottom of the pyrotubes 34a and 34b provides heat during pyrolysis. A blower (not shown) provides forced air-cooling through ducts at the end of pyrolysis to cool the pyrotubes 34a and 34b in preparation for the next aerosol collection cycle.

The mass spectrometer 40 includes a preprogrammed list of molecular patterns. Each molecular pattern on the list is associated with a specific biological agent. If any biological agents are present the sample, the mass spectrometer 40 identifies the biological agents by comparing the identified molecular pattern to the list of molecular patterns preprogrammed into the mass spectrometer 40. After a match is found, the mass spectrometer 40 identifies the associated biological agent.

One detecting device 26a and 26b operates in a sample collection mode when the other detecting device 26a and 26b operates in a sample analysis mode. After a predetermined amount of time, the roles of the detecting devices 26a and 26b are reversed. Therefore, the biological agent detector 20 continuously collects an air sample for analysis. The mode-switching phase lasts approximately 0.5 seconds. During the change-over period, air is still collected. Preferably, the predetermined amount of time is one minute. However, one skilled in the art would know what predetermined amount of time to employ.

As shown in FIG. 4A, the detecting device 26a operates in the sample collection mode, and the detecting device 26b operates in the sample analysis mode. The concentrated aerosol outlet 62 of the bio-concentrator 22 aligns with the detecting device 26a. An exhaust pump 78a draws air through the exhaust line 36a for exhausting to the atmosphere. When the exhaust pump 78a is active, the exhaust pump 78b of the detecting device 26b is inactive and does not exhaust air through the exhaust line 36b. The duration of the sample collection is programmable by software. In one example, the sample is collected for approximately 1 to 5 minutes. One skilled in the art would know how long to collect the sample. A control 87 controls the exhaust pumps 78a and 78b and the motor 70.

The sample lines 38a and 38b meet at a point, and an outlet line 120 extends from the point and directly to the mass spectrometer 40 to define a "T." When detecting device 26a is in sample collection mode and the detecting device 26b is in sample analysis mode, the pressure in detecting device 26a is lower than the ambient, and the pressure in the detecting device 26b is greater than the ambient. There is a net flow of gas from the detecting device 26b to the detecting device 26a.

While the detecting device 26a is operating in the sample-collection mode, a sample previously collected in the pyrotube 34b of the detecting device 26b is analyzed. The methylating reagent is added to the sample in the pyrotube 34b through the injector needle 46b from the reagent source 44b to split open the cells of any bacterial agents in the sample and neutralize and derivatize the organic molecules of the biological agents to form more volatile molecules. The sample in the pyrotube 34b is then pyrolyzed or heated by the heater 58b to form gas molecules. The sample can be pyrolyzed for approximately 1.5 minutes. However, one skilled in the art would know how long to pyrolyze the sample collected in the pyrotube 34b.

The pyrolysis products are directed from the detecting device 26b and along the sample line 38b, the outlet line 120, and directly to the mass spectrometer 40. The detecting device 26b has an internal pressure that is greater than the internal pressure of the detecting device 26a, directing the pyrolysis products from the detecting device 26b to the outlet line 120 and to the mass spectrometer 40. Approximately 1 milliliter per minute of the gas molecules are provided to the mass spectrometer 40.

After the predetermined amount of time, the detecting devices 26a and 26b switch functions. That is, the detecting device 26a then operates in the sample analysis mode, and the detecting device 26b operates in the sample collection mode. The motor 70 rotates the turntable 60 such that the concentrated exhaust outlet 62 of the bio-concentrator 22 aligns with the inlet tube 30b of the detecting device 26b to collect a sample of air in the pyrotube 34b, as shown in FIG. 4B. The sample of air previously collected in the pyrotube 34a of the detecting device 26a is then analyzed.

When the detecting device 26b operates is in sample collection mode and the detecting device 26a operates in the sample analysis mode, the pressure in the detecting device 26b is lower than the pressure in the detecting device 26a. There is a net flow of gas from the detecting device 26a to the detecting device 26b. The gases from the detecting device 26a flows through the "T" and along the outlet line 120 to be directly sampled by the mass spectrometer 40. That is, the pyrolysis products flow along the sample line 38a and along the outlet line 120 to the mass spectrometer 40.

The biological agent detector 20 of the present invention can be used to detect biological agents used in biological warfare, such as anthrax. However, it is to be understood that other biological agents can be detected. Any substance having a unique pattern of fatty acids that can be identified by the mass spectrometer 40 can be detected and identified.

Although detecting devices 26a and 26b are disclosed as being two separate devices, it is to be understood that the detecting devices 26a and 26b could be integrated into a single assembly. In addition, other types of biological agent detectors could be used in place of the pyrolysis/mass spectrometer detector described herein.

The foregoing description is only exemplary of the principles of the invention. Many modifications and variations of the present invention are possible in light of the above teachings. The preferred embodiments of this invention have been disclosed, however, so that one of ordinary skill in the art would recognize that certain modifications would come within the scope of this invention. It is, therefore, to be understood that within the scope of the appended claims, the invention may be practiced otherwise than as specifically described. For that reason the following claims should be studied to determine the true scope and content of this invention.

What is claimed is:

1. A biological agent detection system for detecting a biological agent in an air sample comprising:
   a first detecting device; and
   a second detecting device, wherein the first detecting device operates in a sample collection mode when the second detecting device operates in a sample analysis mode and the first detecting device operates in the sample analysis mode when the second detecting device operates in the sample collection mode, wherein an air sample is collected during the sample analysis mode, and the air sample is analyzed and any biological agents in the air sample are identified during the sample analysis mode, wherein each of the first detecting device and the second detecting device includes an inlet tube, a pyrotube and a heater, the inlet tube draws the aerosol sample into the pyrotube during the sample collection mode, and the heater heats an aerosol sample in the pyrotube during the sample analysis mode.

2. The system as recited in claim 1 further including a bio-concentrator that concentrates the air sample to an aerosol sample, wherein the bio-concentrator is shared by the first detecting device and the second detecting device.

3. The system as recited in claim 2 further including a turntable having a hole, wherein the turntable moves the bio-concentrator between a first position wherein the hole aligns with the first detecting device to direct the aerosol sample to the first detecting device and a second position wherein the hole aligns with the second detecting device to direct the aerosol sample to the second detecting device.

4. The system as recited in claim 1 wherein each of the first detecting device and the second detecting device includes a heated sample line that transports the aerosol sample to a chemical analyzing device for analysis during the sample analysis mode.

5. The system recited in claim 4 wherein a pressure differential internal to the pyrotube of each of the first detecting device and the second detecting device causes a net flow of pyrolysis gas products from one of the first detecting device and the second detecting device that is operating in the sample analysis mode to the other of the first detecting device and the second detecting device that is operating in the sample collection mode and directs the aerosol sample in the one of the first detecting device and the second detecting device that is operating in the sample analysis mode to the chemical analysis device.

6. The system as recited in claim 1 further including a reagent source that contains a methylating reagent, wherein each of the first detecting device and the second detecting device includes an injector needle that injects the methylating reagent into the pyrotube during the sample analysis mode.

7. The system as recited in claim 1 further including a lifting device that biases the pyrotube against a body portion to ensure a gap between a closed end of the pyrotube and the inlet tube is constant.

8. The system as recited in claim 1 further including a ferrule, a body portion and a lifting device that biases the ferrule against the body portion to form a seal that contains the aerosol sample and processed gasses in the pyrotube.

9. The system as recited in claim 1 wherein each of the first detecting device and the second detecting device includes an exhaust line, wherein a portion of the air sample drawn into one of the first detecting device and the second detecting device during the sample collection mode is exhausted through the exhaust line.

10. A biological agent detection system for detecting a biological agent in an air sample comprising:
    a bio-concentrator that concentrates an air sample to an aerosol sample;
    a detecting device including:
      a first detecting device including a first inlet tube that draws the aerosol sample into a first pyrotube when the first detecting device is operating in a sample collection mode, a first injector needle and a first sample line, and
      a second detecting device including a second inlet tube the draws the aerosol sample into a second pyrotube when the second detecting device is operating in the sample collection mode, a second injector needle, and a second sample line, wherein the first detecting device operates in the sample collection mode when the second detecting device operates in a sample analysis mode and the first detecting device operates in the sample analysis mode when the second detecting device operates in the sample collection mode, wherein the air sample is collected during the sample analysis mode, and the air sample is analyzed and any biological agents in the air sample are identified during the sample analysis mode;

a heater to heat the aerosol sample collected in the first pyrotube and the second pyrotube during the sample analysis mode;

a reagent source that contains a methylating reagent, wherein each of the first injector needle and the second injector needle injects the methylating reagent into the first pyrotube and the second pyrotube, respectively, during the sample analysis mode; and a mass spectrometer for identification of any biological agents in the aerosol sample during the sample analysis mode.

11. The system as recited in claim 10 further including a turntable having a hole, wherein the turntable moves the bio-concentrator between a first position wherein the hole aligns with the first detecting device to direct the aerosol sample to the first detecting device and a second position wherein the hole aligns with the second detecting device to direct the aerosol sample to the second detecting device.

12. The system as recited in claim 10 wherein each of the first detecting device and the second detecting device includes an exhaust line, wherein a portion of the aerosol sample drawn into one of the first detecting device and the second detecting device during the sample collection mode is exhausted through the exhaust line.

13. The system as recited in claim 6 wherein the methylating reagent is TMAH.

14. The system as recited in claim 1 wherein the system includes only two detecting devices.

15. The system as recited in claim 3 wherein the aerosol sample passes through the hole when directed from the bio-concentrator to the first detecting device and the second detecting device.

16. The system as recited in claim 3 wherein the first detecting device and the second detecting device are located under the turntable.

17. The system as recited in claim 4 wherein the chemical analyzing device is a mass spectrometer.

18. The system as recited in claim 10 wherein the methylating reagent is TMAH.

19. The system as recited in claim 10 wherein the system includes only two detecting devices.

20. The system as recited in claim 11 wherein the aerosol sample passes through the hole when directed from the bio-concentrator to the first detecting device and the second detecting device.

21. The system as recited in claim 11 wherein the first detecting device and the second detecting device are located under the turntable.

22. A biological agent detection system for detecting a biological agent in an air sample comprising:
a first detecting device;
a second detecting device, wherein the first detecting device operates in a sample collection mode when the second detecting device operates in a sample analysis mode, and the first detecting device operates in the sample analysis mode when the second detecting device operates in the sample collection mode , wherein each of the first detecting device and the second detecting device includes an inlet tube, a pyrotube and a heater, the inlet tube draws the aerosol sample into the pyrotube during the sample collection mode, and the heater heats an aerosol sample in the pyrotube during the sample analysis mode; and
a reagent source that contains a methylating reagent, wherein the methylating reagent is added to one of the first detecting device and the second detecting device during the sample analysis mode.

\* \* \* \* \*